(12) United States Patent
Jensen

(10) Patent No.: US 11,400,229 B2
(45) Date of Patent: Aug. 2, 2022

(54) DRUG DELIVERY SYSTEM WITH DOSE CAPTURING

(71) Applicant: Novo Nordisk A/S, Bagsvaerd (DK)

(72) Inventor: Peter Lundholm Jensen, Copenhagen (DK)

(73) Assignee: Novo Nordisk A/S, Bagsvaerd (DK)

(*) Notice: Subject to any disclaimer, the term of this patent is extended or adjusted under 35 U.S.C. 154(b) by 770 days.

(21) Appl. No.: 16/095,837

(22) PCT Filed: Apr. 28, 2017

(86) PCT No.: PCT/EP2017/060292
§ 371 (c)(1),
(2) Date: Oct. 23, 2018

(87) PCT Pub. No.: WO2017/186955
PCT Pub. Date: Nov. 2, 2017

(65) Prior Publication Data
US 2021/0220563 A1 Jul. 22, 2021

(30) Foreign Application Priority Data
Apr. 29, 2016 (EP) .................................. 16167814

(51) Int. Cl.
*A61M 5/315* (2006.01)
(52) U.S. Cl.
CPC .... *A61M 5/31553* (2013.01); *A61M 5/31568* (2013.01)

(58) Field of Classification Search
CPC ...................... A61M 5/31553; A61M 5/31568
See application file for complete search history.

(56) References Cited

U.S. PATENT DOCUMENTS

| 6,482,185 | B1 | 11/2002 | Harlmnann | |
| 6,585,698 | B1* | 7/2003 | Packman | G16H 20/17 604/207 |

(Continued)

FOREIGN PATENT DOCUMENTS

| CN | 104918649 A | 9/2015 |
| CN | 105194766 A | 12/2015 |

(Continued)

*Primary Examiner* — Dung T Ulsh
(74) *Attorney, Agent, or Firm* — Wesley Nicolas

(57) ABSTRACT

Drug delivery system comprising expelling means for expelling an amount of drug from a reservoir, the expelling means comprising dose setting means (11, 21, 122) allowing a user to set a dose to be expelled, and actuation means (123) for releasing the drug expelling means to expel the set dose. The dose setting means comprises a drive sleeve (22) adapted to be rotated to set a dose, and a rotatable driven member (21) arranged for being rotationally driven by the drive sleeve (22) in a slaved rotational movement by means of a torque transfer coupling between the drive sleeve (22) and the rotatable driven member (21). The system further comprises an electronically controlled capturing system for capturing data representing a property related to the amount of drug expelled from the reservoir by the expelling means, and switch means configured to initiate an action within the electronically con-trolled capturing system upon occurrence of the slaved rotational movement.

25 Claims, 2 Drawing Sheets

(56) References Cited

U.S. PATENT DOCUMENTS

| | | | |
|---|---|---|---|
| 6,666,849 B1* | 12/2003 | Marshall | A61M 5/31553 604/131 |
| 9,623,188 B2 | 4/2017 | Nielsen et al. | |
| 10,195,359 B2 | 2/2019 | Pedersen et al. | |
| 10,376,644 B2 | 8/2019 | Krusell et al. | |
| 10,434,260 B2 | 10/2019 | Steel et al. | |
| 2009/0318865 A1 | 12/2009 | Moller et al. | |
| 2012/0072236 A1* | 3/2012 | Atkin | G16H 10/65 705/3 |
| 2014/0194829 A1* | 7/2014 | Baek | A61M 5/31551 604/207 |
| 2015/0018775 A1* | 1/2015 | Groeschke | A61M 5/31551 604/207 |
| 2016/0213853 A1* | 7/2016 | Despa | A61M 5/31568 |
| 2017/0182258 A1* | 6/2017 | Michael | A61M 5/31568 |
| 2017/0189625 A1* | 7/2017 | Cirillo | A61M 5/5086 |
| 2017/0354779 A1* | 12/2017 | Atterbury | A61M 5/2455 |
| 2018/0008778 A1* | 1/2018 | Erbstein | A61M 5/31568 |

FOREIGN PATENT DOCUMENTS

| | | |
|---|---|---|
| CN | 105102023 B | 5/2019 |
| DE | 29904864 | 8/2000 |
| EP | 2060284 A1 | 5/2009 |
| JP | 2014520584 A | 8/2014 |
| JP | 2015517856 A | 6/2015 |
| WO | 2010052275 A2 | 5/2010 |
| WO | 2010/098927 A1 | 9/2010 |
| WO | 2010098928 A1 | 9/2010 |
| WO | 2010/128493 A2 | 11/2010 |
| WO | 2013004843 A1 | 1/2013 |
| WO | 2014161955 A1 | 10/2014 |
| WO | 2015075134 A1 | 5/2015 |
| WO | 2015185687 A1 | 12/2015 |
| WO | 2016062807 A1 | 4/2016 |

* cited by examiner

DRUG DELIVERY SYSTEM WITH DOSE CAPTURING

CROSS-REFERENCE TO RELATED APPLICATIONS

This application is a 35 U.S.C. § 371 National Stage application of International Application PCT/EP2017/060292 (published as WO 2017/186955), filed Apr. 28, 2017, which claims priority to European Patent Application 16167814.9, filed Apr. 29, 2016, the contents of all above-named applications are incorporated herein by reference.

The present invention relates to a system for capturing drug delivery dose data. Especially, the invention relates to generation of an activation signal for initiating an action in response to user operation of a drug delivery system.

BACKGROUND OF THE INVENTION

In the disclosure of the present invention reference is mostly made to the treatment of diabetes by delivery of insulin, however, this is only an exemplary use of the present invention.

Drug Injection devices have greatly improved the lives of patients who must self-administer drugs and biological agents. Drug Injection devices may take many forms, including simple disposable devices that are little more than an ampoule with an injection means or they may be durable devices adapted to be used with pre-filled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, from the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of ejection information from medication delivery systems.

Though some injection devices integrate this monitoring/acquisition mechanism into the device itself, e.g. as disclosed in US 2009/0318865 and WO 2010/052275, most devices of today are without it. The most widely used devices are purely mechanical devices either durable or prefilled. The latter devices are to be discarded after being emptied and so inexpensive that it is not cost-effective to build-in electronic data acquisition functionality in the device it-self. Correspondingly, data acquisition/monitoring functionality have been proposed to be provided in a separate device to be put on or in the injection device, i.e. some kind of accessory e.g. an add-on module to the injection device.

For example, WO 2010/098927 discloses a medical module which is configured to be attached to a drug delivery pen, the module being adapted to detect and store selected and ejected dosages as well as other data. Further arrangements adapted to capture dose data are known from WO 2010/128493, EP 2 060 284, WO 2010/052275 and WO 2013/004843.

Some injection devices/systems which incorporate electronic circuitry require a separate initial action from the user, such as operation of a power button, to switch-on electronics of the electronic circuitry in order to enable electronic detection that a user operable member, such as a rotatable operable member, is in fact operated. Typically, such devices include several operable members making the devices and their user interface unnecessary complex.

Having regard to the above, it is an object of the present invention to provide systems and methods supporting simple and reliable yet cost- and energy-effective detection and storage of dose data related to use of a drug delivery device.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a drug delivery system is provided, comprising expelling means for expelling an amount of drug from a reservoir, the expelling means comprising (a) dose setting means allowing a user to set a dose amount of drug to be expelled, and (b) actuation means for releasing or driving the drug expelling means to expel the set dose amount. The system further comprises an electronically controlled capturing system for capturing data representing a property related to the amount of drug expelled from a reservoir by the expelling means, and switch means coupled to the electronically controlled capturing system wherein operation of the switch means initiates an action within the electronically controlled capturing system. The dose setting means comprises (a) a drive sleeve adapted to be rotated to set a dose, and (b) rotatable driven member, such as a driven sleeve, arranged for being rotationally driven or slaved by the drive sleeve, wherein a torque transfer coupling is arranged between the drive sleeve and the rotatable driven member for transferring rotational movement from the drive sleeve to the rotatable driven member. The switch means are coupled to the drive sleeve and the rotatable driven member. The torque transfer coupling is adapted to allow limited independent rotational movement of the drive sleeve relative to the rotatable driven member to operate the switch means to provide said action.

As the torque transfer coupling is arranged between the drive sleeve and the rotatable driven member, and due to the limited independent rotational movement of the drive sleeve relative to the rotatable driven member, the drive sleeve is prevented from rotating independently from the rotatable driven member beyond a predefined degree, so that the rotatable driven member is rotationally slaved by rotational movement experienced by the drive sleeve. Due to said slaved rotation, a slight delay in rotational movement of the rotatable driven member is experienced upon operation of the drive sleeve, i.e. during a user's manipulation of the dose setting means. This enables early detection of operation of the dose setting means enabling the switch arrangement to cause an action within the electronically controlled capturing system. In this way, a reduction in the number of required user operable members, such as knobs, buttons or other control elements, is enabled.

As non-limiting examples, said data representing a property related to the amount of drug expelled from a reservoir may comprise one or more of the following; a set dosage amount, an expelled dosage amount, time information relating to the occurrence of a dose setting activity and time information relating to the occurrence of a dose expelling activity.

In particular embodiments of the invention, when providing a data capture system, it should be secured that the system is operational in good time before the system shall make its data acquisition (of e.g. positional information relating to the set dose amount) in order to get the electronics ready for the measurement(s). Initialization may include power-up time for the electronics of a fully or partly dormant system, the time for initializing the electronics or the necessary time for the electronics to make a reliable measuring/data acquisition. By the above arrangement an energy-effective system is provided which is energized just prior to the dose setting means has been dialed away from an initial dose setting position, yet sufficiently early to allow the electronic data capture system to capture data relating to the initial setting.

In some embodiments the drug delivery system is provided as an injection device comprising a dose setting and expelling mechanism where the mechanism does not incorporate an electrically driven motor. The dose setting means may typically comprise a rotatable dose setting component that is rotated during dose setting, wherein the position of the dose setting member defines the amount of drug to be expelled during drug expelling, and wherein the dose setting component moves as the rotatable driven member is rotated relative to other structure, e.g. a housing.

In some embodiments, the drug delivery system may be provided as an injection device in the form of an injection pen or it may comprise an injection pen.

The drug delivery system may comprise an identifier associated with an indicator portion which moves (e.g. rotationally) during dose setting and represents a property related to the amount of drug expelled from a reservoir by the expelling means when the set dose is expelled, the detection means being adapted to capture the identifier. The detection means may be in the form of optical sensor means adapted to capture values represented by the identifier, however, this type of sensor being a non-limiting example.

Other means for communicating and capturing data related to dose size may be implemented. For example, the pen may be provided with electronic means generating a wireless signal to be captured by the capturing system, it may be provided with magnetic means or the pen may produce an audible signal to be captured by the capturing system.

In an exemplary embodiment the drug delivery system comprises a drug delivery unit and a data capture unit releasably attachable to each other, the drug delivery unit comprising the drug expelling means, part of the dose setting means, and the actuation means, whereas the data capture unit comprises the electronically controlled capturing system, remaining parts of the dose setting means and the switch means. The drug delivery unit may include a dose dial member.

The dose setting means may comprise a rotatable dose dial member, wherein the position of the dose dial member is representative for the amount of drug to be expelled, and wherein the dose dial member moves as the rotatable driven member is rotated. In some embodiments, the rotatable driven member is provided in the form of the dose dial member. In other embodiments, the rotatable driven member is attached to a dose dial member such that the two parts are configured to rotate together in unison.

In some embodiments the rotatable driven member is rotatable in a first rotational direction to dial up a dose and rotatable in a second rotational direction counter to the first rotational direction in order to dial down an initially set dose.

In some embodiments the rotatable driven member is arranged for rotation about an axis and wherein the drive sleeve is arranged coaxially with the rotatable driven member for rotation about said axis. In other embodiments, the drive sleeve and the rotatable driven member rotates around respective different axes.

The system may be so configured that rotation of the rotatable driven member requires exertion of a torque level above a first threshold torque and wherein said limited independent rotational movement requires exertion of a torque less than said first threshold torque.

In some embodiments the dose setting means defines a dose increment mechanism configured to provide for rotational movement of the rotatable driven member in discrete rotational steps through a multitude of rotational rest positions for the rotatable driven member. In certain configurations, the rotatable driven member may be configured as a multi-turn rotatable component meaning that the rotatable driven member is rotatable for more than 360 degrees rotation from a minimum dose setting to a maximum dose setting. In particular embodiments, the dose increment mechanism is configured for rotational movement of the rotatable driven member in dose steps in the order of 5-45 degrees, such as in the order of 5-15 degrees.

In some embodiments, the switch means is configured for starting initialization of the capturing system. In some embodiments, the capturing system is allowed to initialize during the rotatable driven member's movement from an initial dose setting position to a neighbouring dose setting position. In other embodiments, the switch means is configured for providing electrical signals used for shifting or modifying electronic settings or parameters of the electronically controlled capturing system upon making or breaking of contacts within the switch means. The drive sleeve may in some embodiments be provided as a manually grippable sleeve member which is directly manipulated by the hand of a user. In some embodiments the switch means comprises one or more on-off switches. In other embodiments, the switch means may be configured for recording a level of torque being applied onto the drive sleeve. The dose setting means may be so configured that a torque of a first magnitude are required to be exerted onto the rotatable driven member for movement of the rotatable driven member from a first rest position to a second neighbouring rest position and wherein said switch means is configured to be operated for switching by exertion of a torque onto the drive sleeve of second magnitude less than said torque of first magnitude.

The system may be so configured that upon increasing rotational torque onto the drive sleeve, exerted by the hand of a user, the capturing system is allowed to initialize in the course of an increase in rotational torque from said torque of second magnitude to said torque of first magnitude.

In some embodiments the drive sleeve defines a pre-defined rotational rest position relative to the rotatable driven member and wherein the drive sleeve is rotationally movable relative to the rotatable driven member in at least one rotational direction away from said pre-defined rotational rest position to a rotational limit stop position by a movement less than 25 degrees, such as less than 10 degrees, such as less than 8 degrees, such as less than 6 degrees, such as, such as less than 4 degrees, or such as less than 2 degrees. Hence, the drive sleeve is prevented from rotating further relative to the rotatable driven member from the rotational rest position than the respective rotational movements referred to above.

In other embodiments, the pre-defined rotational rest position is a pre-defined central rotational rest position and wherein the drive sleeve is movable relative to the rotatable driven member in either rotational direction away from said pre-defined central rotational rest position to a rotational limit stop position by a movement less than 25 degrees, such as less than 10 degrees, such as less than 8 degrees, such as less than 6 degrees, such as less than 4 degrees, and such as less than 2 degrees.

In some embodiments, the drive sleeve is movable relative to the rotatable driven member in either rotational direction away from said pre-defined central rotational rest position to a rotational limit stop position by a rotational movement of at least 1 degree.

In some forms, a biasing means is arranged between the drive sleeve and the rotatable driven member and configured so that the drive sleeve is rotationally biased relative to the rotatable driven member towards the pre-defined rotational rest position, e.g. the central rotational rest position.

The drug expelling means (or mechanism) may be of the type in which a spring is loaded during setting of a dose, this allowing spring-driven drug expelling when the set and loaded mechanism is released by the user, this allowing a design in which the release (and actuation) button is axially stationary during dose setting. Alternatively, the drug delivery system may be of the traditional type in which a member is dialed proximally to set a dose and subsequently moved distally to expel the set dose. In such a system the expelling means can be said to be driven when the member starts to be moved distally.

In some embodiments the drug delivery system comprises a drug delivery unit and a data capture unit releasably attachable to each other. The drug delivery unit may comprise:
    the drug expelling means,
    the actuation means, and
    a rotatable dose dial member,
    whereas the data capture unit may comprise:
    the drive sleeve,
    the rotatable driven member,
    the electronically controlled capturing system, and
    the switch means,
    wherein, when the drug delivery unit and the data capture unit are attached to each other, the rotatable driven member couples rotationally with the rotatable dose dial member so that the dose dial member rotates with the rotatable driven member.

The drug delivery unit comprises a housing relative to which the rotatable dose dial member is rotated for setting the amount of drug that is to be expelled. In some forms, the data capture unit attaches exclusively to the rotatable dose dial member of the drug delivery unit. In other embodiments a fixation component of the data capture unit attaches to the housing of drug delivery unit.

In still other embodiments, the drug delivery unit and data capture unit are arranged so as to be permanently fixed to each other, i.e. non-removable, so as to provide a single integral device. In such single integral device a dose dial grip member of the device performs as a drive sleeve, whereas an internal rotatable component, whose position is representative for the amount of drug to be expelled, performs as a rotatable driven member or driven sleeve wherein the torque transfer coupling couples rotation of the dose dial grip member with slaved and delayed rotation of the internal rotatable component.

The drug delivery system may be so configured that the data capture unit further comprises a display means adapted to display a value or condition corresponding to the captured data. Alternatively, or in addition, the drug delivery system may be so configured that the data capture unit further comprises data communication means, such as wireless communication means, for transferring data captured by the data capture unit to an external device. In some forms of the data capture unit that comprises data communication means, the data capture unit comprises no electronically controlled display. Further, for such a data capture unit, in some embodiments, the data capture unit comprises said drive sleeve, and optionally an actuation button to cooperate with the actuation means of the drug delivery unit, but comprises no further user operable members, such as buttons or knobs.

The drug delivery system may be configured to expel a single or a multitude of doses of drug from a held drug reservoir, such as a piston equipped drug cartridge or syringe.

In a further aspect a drug delivery system is provided comprising a drug delivery unit comprising drug expelling means for expelling an amount of drug from a reservoir, the drug expelling means comprising setting means allowing a user to set a dose amount to be expelled from a drug reservoir, and actuation means for releasing or driving the drug expelling means to expel the set dose amount. The drug delivery system further comprises a data capture unit releasably attachable to the drug delivery unit (e.g. of the type described above), the data capture unit comprising an electronically controlled capturing system for capturing data representing a property related to the amount of drug which has been set and/or expelled from the reservoir by the expelling means. In some forms the data representing a property related to the amount of drug is the volume of drug to be expelled by the expelling means.

The drug delivery system may comprise a drug reservoir. For the above-described aspects and embodiments, the drug delivery system may be pre-filled comprising a drug reservoir not intended to be replaced after it has been emptied, or the system may be configured to receive a drug reservoir in the form of a replaceable drug cartridge, e.g. comprising a cartridge holder.

In a yet further aspect a drug delivery system is provided comprising a main portion comprising drug expelling means for expelling drug from a reservoir through an outlet. The drug delivery system further comprises a self-contained add-on data capture module that serves as a tag device adapted to display information relating to the use of the drug delivery system, the tag device comprising a display, and controller means for controlling the display to display information in accordance with the captured data. In yet further aspects, a drug delivery system is provided comprising a main portion comprising drug expelling means for expelling drug from a reservoir through an outlet. The drug delivery system further comprises a self-contained add-on data capture module having communication means configured for transmitting information to an external device in accordance with the captured data.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of the exemplary embodiments reference will be made to the use of insulin.

BRIEF DESCRIPTION OF THE DRAWINGS

In the following the invention will be further described with reference to the drawings, wherein FIG. 1 schematically shows a proximal portion of a pen-type drug delivery device, FIG. 2 schematically shows a first embodiment of a drug delivery system according to the invention comprising a drug delivery device and an add-on data capture unit attached relative to each other, FIG. 3 schematically shows two perspective views of the first embodiment of a drug delivery system, wherein the left view shows the system in a neutral state and wherein the right view shows the system in a state where a dose setting procedure has been initiated, FIG. 4 schematically shows details of a switch arrangement of the data capture unit of FIG. 2.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only.

Figure 1:
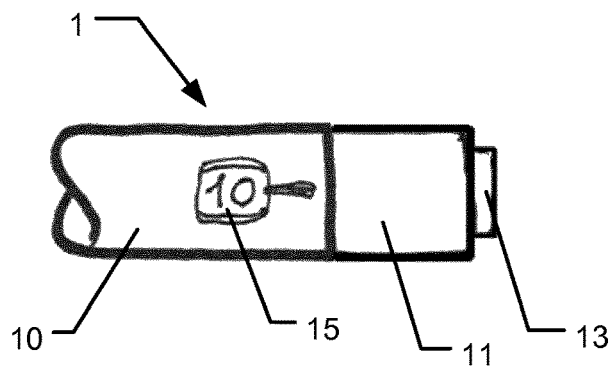

FIG. 1 schematically shows the proximal portion (i.e. comprising a dose setting and mechanical expelling mechanism but not a drug reservoir or cartridge) of a traditional pen-formed drug delivery device as used typically for administration of insulin. The shown embodiment represents the type of pen in which a spring is loaded during setting of a dose, this allowing spring-driven drug expelling when the set and loaded mechanism is released by the user, this allowing a design in which the release (or actuation) button is axially stationary during dose setting. A more detailed description of such a pen can be found in e.g. US 2009/054839, US 2008/306446 and US 2008/234634 which are hereby incorporated by reference.

More specifically, FIG. 1 shows a drug delivery device 1 of the pen type comprising a proximal part having a mainly cylindrical housing portion 10 with an expelling mechanism and a distal portion (see FIG. 6) comprising a drug cartridge with an axially moveable piston driven by the expelling mechanism. The pen device 1 comprises a rotatable dose dial member 11 allowing a user to set and adjust (i.e. dial-up and dial-down) a variable dose size of given increments (e.g. 1 IU insulin) to be expelled from the cartridge, the actual dose size (e.g. 25 IU insulin) being indicated by numbers shown in a window 15, the numbers being arranged on a rotating dose drum member. The maximum amount of drug that can be delivered during one out-dosing is defined by the injection device. For example the injection device may deliver variable dose amounts during one out-dosing between 1 IU insulin and 80 IU insulin.

The dose dial member 11 used for setting a dose is connected to a dose increment mechanism configured to provide for rotational movement of the dose dial member 11 in discrete rotational steps through a multitude of rotational rest positions for the dose dial member relative to the housing of the device. The dose dial member 11 may be rotated between a minimum dose rotational position and a maximum dose rotational position and be rotated in either direction away from a present dose setting to dial up or dial down an initial set dose.

A user-operated actuation member defining a release member in the form of push button 13 is arranged at the proximal end and adapted to release the expelling mechanism when pushed distally by the user. As the mechanism is released the set dose will be expelled from the cartridge and the dose drum will correspondingly rotate back to its initial zero position. If the mechanism is designed to stop expelling when the user stops pushing the release button, the number display in the window will show the portion of the dose (e.g. the numbers of units) not yet expelled, e.g. 10 units of insulin.

Based on the above pen design, an electronic data acquisition system could be based on the following concept: To save energy the system is dormant during non-use of the device, i.e. the system automatically enters into a sleep-mode when not being used. When the dose is set by rotating the dose dial member this indicates to the system that the dose setting and/or the expelled dose is to be captured. Typically, data representing the initial position of the mechanism before it starts moving are required, because the initial position in some instances can be different from the position observed before the sensory system went to sleep. However, depending on the principle used to capture information about the set and/or expelled dose, the system may need time to "wake up" and capture dose information such as dose amount and/or time information that relates to a drug administration.

Figure 2:
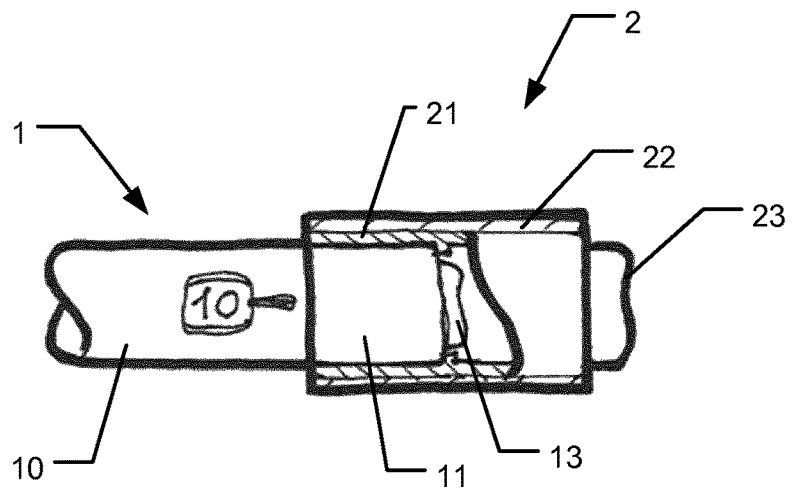
Figure 3:
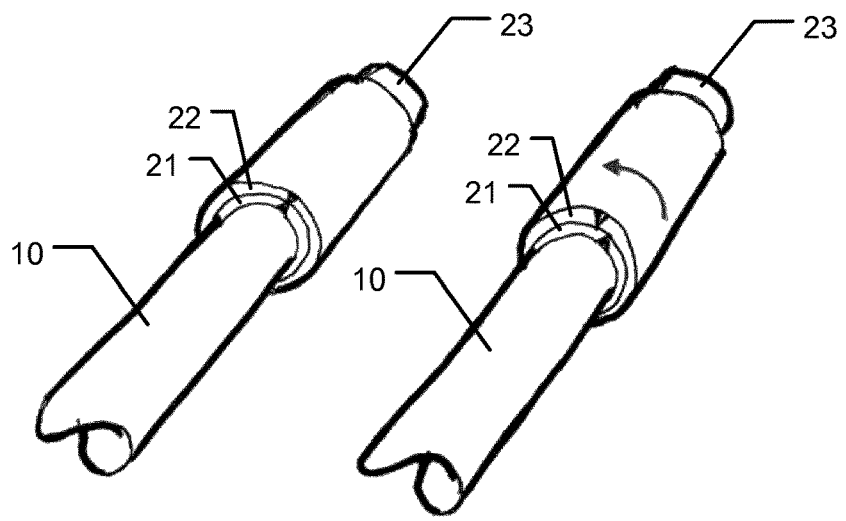
Figure 4:
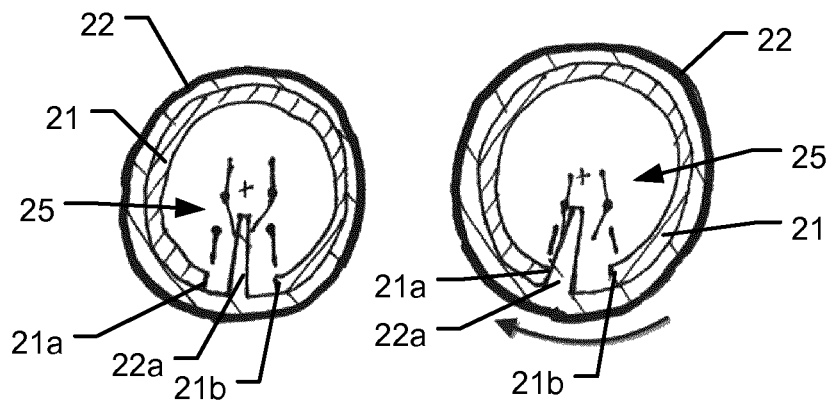

Addressing the above issue, FIGS. 2 to 4 schematically show different views of a first embodiment in which a pen device 1 of the type shown in FIG. 1 is provided with an add-on data capture module 2 (or unit) providing additional "wake-up time" when a dose setting procedure is initiated. In the shown embodiment the add-on module 2 comprises an inner sleeve 21 adapted to releasably engage the dose dial member 11 of the pen device so that, whenever the add-on data capture module 2 is attached to the pen device 1, the dose dial member 11 follows rotation of the inner sleeve 21. The add-on module 2 further comprises an outer sleeve 22 arranged concentrically with the inner sleeve 21 and the dose dial member 11, electronic detection means (not shown), and a secondary user-operated actuation member (in the form of push-button 23) which couples to the push button 13 of the pen device so that pushing button 23 causes the push button 13 to be pushed in. In the first embodiment, the add-on data capture module 2 is provided as a unit that releasably couples to the pen device 1 so that the add-on data capture module may be attached to a first pen device with the option of later switching the add-on data capture to cooperate with second and further pen devices.

A way to achieve a wake up signal is by making the outer sleeve 22 connected to an internal switch arrangement accommodated within the add-on data capture module 2. When the user rotates the outer sleeve 22 to set a dose, the outer sleeve will move independently for a limited movement, such as a few degrees, before engaging with a stop and then carry the inner sleeve 21 with it in a rotational movement thereby causing the dose dial member 11 to rotate as well. The small independent movement of the outer sleeve 22 relative to the inner sleeve 21 is used to activate the internal switch arrangement. This will enable the electronics of the add-on data capture module 2 to initialize before the dose dial member 11 is rotated away from the initial position, thereby enabling data capture of the initial position of the dose dial member 11.

Referring to FIGS. 2 and 3, as long as the data capture module 2 is attached to the pen device 1, the outer sleeve 22 performs as a dose dial grip for rotationally operating the dose dial member 11 of the pen device. A torque transfer coupling couples rotational movement of the outer sleeve 22 with rotational movement of inner sleeve 21 although a limited degree of relative rotational movement is possible between the outer sleeve 22 and the inner sleeve 21. In the context of certain embodiments of the present invention, such as in the embodiment shown in FIGS. 2-4, the outer sleeve 22 may perform as a drive sleeve whereas the inner sleeve 21 may perform as a rotatable driven member or a driven sleeve which is rotationally driven by the drive sleeve, i.e. the rotatable driven member is slaved by the drive sleeve.

In the shown embodiment, although not shown in the figures, a spring arrangement or action is provided between the outer sleeve 22 and the inner sleeve 21 which urges the outer sleeve towards a neutral rotational position relative to the inner sleeve. The neutral rotational position of the outer sleeve 22 is a pre-defined central rotational rest position relative to inner sleeve 21. The spring arrangement thus provides a rotational bias allowing the outer sleeve to be moved against the bias, and relative to the driven sleeve in either rotational direction, away from said pre-defined central rotational rest position relative to the inner sleeve 22 to a rotational limit stop position. In the shown embodiment, an internal rib or protrusion 22a of the outer sleeve 22 cooperates with hard stops 21a and 21b of the inner sleeve 21 to provide the limit stop positions. In other embodiments, hard stops are not required, and the limit stop positions may be provided by the spring arrangement. Either the hard stops 21a and 21b or the not shown spring arrangement serve as a torque transfer coupling between the outer sleeve and the inner sleeve to make the inner sleeve follow rotation of the outer sleeve relative to the housing of the cause the inner sleeve to be slaved by the outer sleeve to perform rotational movement The left-hand view of FIG. 3 shows the drug delivery system in a state where no external forces act on the outer sleeve 22 and the outer sleeve is in the neutral rotational position (notice the two triangular points on the two sleeves). In the right-hand view of FIG. 3 a rotational torque has been provided on the outer sleeve 22 acting in the rotational direction indicated by the arrow. The inner triangular point indicates that the inner sleeve 21 has not rotated yet relative to the pen device 1, although the outer sleeve 22 has been rotated away from the neutral rotational position.

FIG. 4 shows schematically cross sectional views corresponding to the respective views of FIG. 3. In the view of FIG. 4 a switch arrangement of the data capture module 2 is visible. It is further shown that the outer sleeve 22 includes a rib or protrusion 22a which protrudes radially inwards and is adapted to engage a switch arrangement 25 arranged within the data capture module 2. The switch arrangement 25 is arranged to detect if the outer sleeve has been moved rotationally to a pre-defined extent away from the neutral rotational position at either side thereof. If increasing torque is exerted onto the outer sleeve 22 to rotate it even further, rotational stop limits (non-referenced) prevent the outer sleeve from rotating further away from the neutral rotational position. In the embodiment shown in FIG. 4, the switch arrangement 25 is provided as an on-off switch at either side symmetrically to the neutral rotational position. The switch arrangement may be connected to pull-up resistor(s) for providing a detectable shift in voltage when the outer sleeve 22 is rotated away from the neutral rotational position relative to the inner sleeve 21. The relative rotational position wherein the contacts of the switch arrangement make or break may be provided at a rotational position which is situated in spaced relationship relative to the respective rotational stop limit.

The spring constant of the spring arrangement is so selected that the outer sleeve 22 starts to move rotationally relative to the inner sleeve 21 enabling the switch arrangement to be activated before the reluctance of the dose increment mechanism against dialing away from the present dose setting is overcome.

In the left-hand view of FIG. 4, the contacts have not been closed indicating that the outer sleeve 22 has not been rotated away from the neutral rotational position. If the data capture module 2 is in sleep-mode, the status of the contacts means that the data capture module will remain in sleep-mode. However, as shown in the right-hand view of FIG. 4, the outer sleeve 22 has been initially rotated slightly relative to the inner sleeve 21 causing the contacts to make and thus provide a signal that is used for starting initialization of the capturing system. However, as the inner sleeve 21 has not yet been rotated away from the initial position, the capturing of the initial position of the dose dial member 11 is enabled. Increasing the applied torque even further on the outer sleeve 22 this will make the inner sleeve 21 (being rotationally coupled with the dose dial member 11) rotate for increasing or decreasing the dose to be delivered by the pen device 1.

As the applied torque exerted onto the outer sleeve 22 is increased the rotational torque on the inner sleeve 21 is raised which, at some point, overcomes the reluctance of the dose dial member 11 to be moved an increment in accordance with the increment mechanism. Hence the applied torque on outer sleeve 22 causes the dose dial member 11 to rotate in accordance with the increment mechanism and a dose is thus either dialed up or dialed down depending on the rotational direction of the applied torque.

In the shown embodiment, the switch arrangement may be arranged as on-off switches. However, in other embodiments, the switch arrangement may be designed to provide a measure of the level of torque that is applied onto outer sleeve 22 relative to the inner sleeve 21. Also, the switch arrangement may be designed to provide information as to the direction of the applied torque.

When torque is applied to the outer sleeve 22 relative to the housing 10 of the pen device 1, the following happens:
1. the outer sleeve 22 of the device rotates,
2. the device switch arrangement 25 is activated,
3. the outer sleeve 22 hits a rotational stop against the inner sleeve 21, and
4. as the user increases the applied torque, the dose dial member 11 starts to rotate together with the inner sleeve 21 and a dose is set on the pen device 1.

As mentioned above the outer sleeve 22 is spring loaded such that, when the user releases the torque from the outer sleeve, the outer sleeve rotates back to the neutral rotational position, in which the switch arrangement is deactivated.

The spring action may be provided in various different ways, non-limiting examples including a separate spring member, utilizing elastic materials of the outer sleeve or inner sleeve or of components engaged with the outer sleeve and inner sleeve, or by using magnetic effects.

With this mechanism incorporated into the data capture module 2, a signal is produced every time the user initiates a procedure for setting or resetting a dose on the pen device which may be utilized for different purposes, such as for starting initialization of the capturing system. However, other embodiments may utilize signals from the switch arrangement for signalling when a user releases the grip on the outer sleeve.

In still other embodiments, the switch arrangement provides a measure of torque exerted on the outer sleeve and may thus indicate that a user attempts to increase a set dose which exceeds the dose volume that remains available in the drug cartridge, as limited by a so-called end-of-content stop mechanism. Such information may be captured by the data capture module 2 and stored for later retrieval and for user guidance about the status of the pen device, such as signalling that the drug cartridge only contains a part of a desired dose and that the user needs to change a drug reservoir or shift to a new pre-filled pen device. The information may alternatively be used, when stored by the data capture module 2, to aid in presenting doses that have been performed as a "split-dose" (i.e. administered as two separate partial dose administrations from two consecutive drug cartridges) and presenting such information as a single dose administration.

In accordance with the above, the switch arrangement may be designed to work both rotational directions, so a switch is activated whether the user turns the dial clockwise or counter clockwise. However, in other embodiments, the switch arrangement may be designed only to detect rotation of the outer sleeve in a single direction away from the neutral rotational position.

Figure 5:
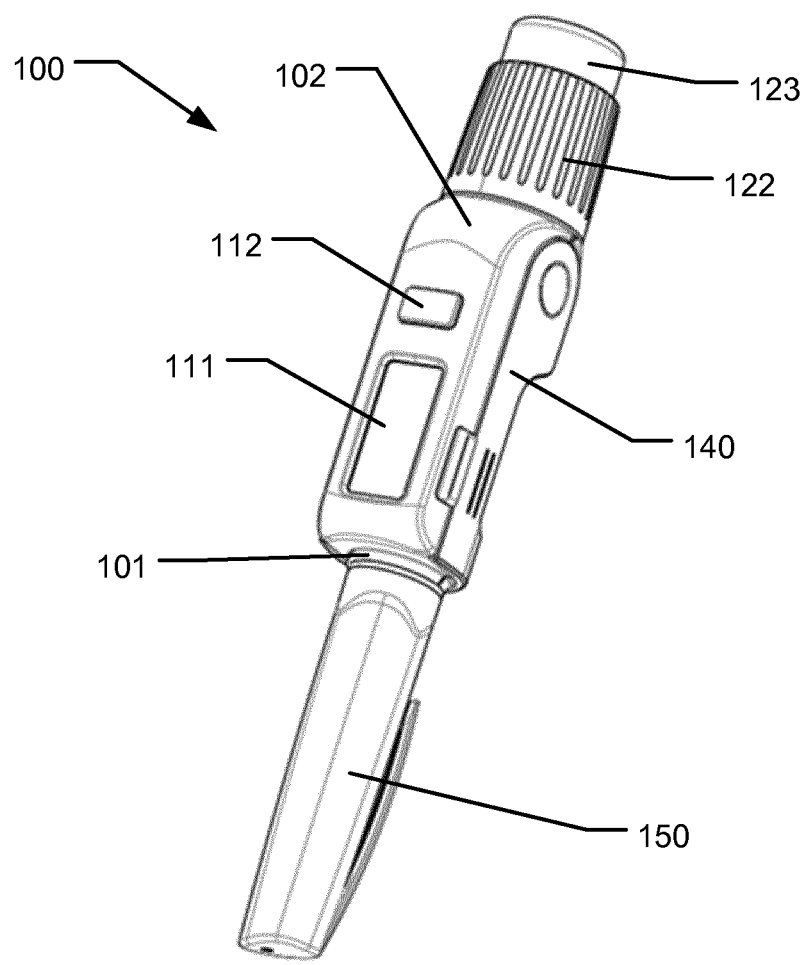
FIG. 5 shows a second embodiment of a drug delivery system according to the invention comprising a drug delivery device and an add-on data capture unit attached relative to each other.

FIG. 5 shows an second embodiment drug delivery system having an overall structure and functionality that resembles the prior art system disclosed in FIG. 5 of WO2013/004843, this reference hereby being incorporated by reference. The drug delivery system comprises a pen-formed drug delivery unit 101 and a data capture unit 102 releasably attachable to each other. However, the figure could also represent a drug delivery device comprising integrated data capture means, i.e. where the data capture unit 102 is non-removably arranged relative to the drug delivery unit 101. The drug delivery unit per se could be of any desirable design providing the necessary input to the data capture unit, however, the shown embodiment represents the type of pen in which a spring is loaded before or during setting of a dose, this allowing spring-driven drug expelling when the set and loaded mechanism is released by the user, this allowing a design in which the release (or actuation) button is axially stationary during dose setting. As previously mentioned, a more detailed description of such a pen can be found in e.g. US 2009/054839, US 2008/306446 and US 2008/234634.

More specifically, such a drug delivery device of the pen type 101 comprises a proximal part having a mainly cylindrical housing portion with an expelling mechanism and a distal portion comprising a drug cartridge with an axially moveable piston driven by the expelling mechanism. The pen comprises a rotatable dose dial member allowing a user to set and adjust (i.e. dial-up and dial-down) a variable dose size of given increments (e.g. 1 IU insulin) to be expelled from the cartridge, the actual dose size (e.g. 25 IU insulin) being indicated by numbers shown in a window, the numbers being arranged on a rotating dose drum member. The maximum amount of drug that can be delivered during one out-dosing is defined by the injection device. For example the injection device may deliver variable dose amounts during one out-dosing between 1 IU insulin and 80 IU insulin. A push button is arranged at the proximal end and adapted to release the expelling mechanism when pushed distally by the user. As the mechanism is released the set dose will be expelled from the cartridge and the dose drum will correspondingly rotate back towards its initial zero position. If the mechanism is designed to stop expelling when the user stops pushing the release button, the number display in the window will show the portion of the dose (e.g. the numbers of units) not yet expelled, e.g. 10 units of insulin.

Based on a drug delivery pen of the type described above FIG. 5 thus shows an embodiment of a drug delivery system 100 comprising a pen-formed drug delivery unit 101 and a data capture unit 102 the units being releasably attachable to each other. The data capture unit 102 comprises a housing 140 that attaches to the housing of the drug delivery unit. The system comprises a rotatable dose dial grip 122 and a proximally arranged release button 123 adapted to be moved between an initial position, and an actuated position in which the expelling means is actuated to expel the set dose. The distal reservoir part of the drug delivery device is covered by a cap member 150. The data capture unit 102 comprises electronic detection means for capturing data representing a property related to the amount of drug as set or expelled from the reservoir by the expelling means, and switch means for starting initializing of data capture, the switch means being actuated when the dose dial grip 122 is rotated away from an initial neutral rotational position. The electronic detection means may incorporate any type of sensor configuration known in the art, and will not be described further herein. The data capture unit may also comprise a display 111 e.g. adapted to show the instant dose setting adjustment, the time and dose size for the last expelling action, etc. The data capture unit may also comprise a key 112 allowing a user to e.g. toggle between a number of recent time-dose logs. The data capture unit may further be provided with an output port for wired or wireless upload of data to an external device, e.g. to the users smartphone or a doctors personal computer.

The functionality described in connection with the first embodiment is incorporated in the drug delivery unit 101 and the data capture unit 102. The inclusion of a switch arrangement similar to the switch arrangement 25 described above allows the controlled capturing system of the data capture unit 102 to initialize and wake up upon the user attempting to dial away from the current dose setting of the drug delivery unit 101.

In other embodiments the switch arrangement and the configuration of the drive sleeve and the rotatable driven member may be configured for purposes other than initializing a dormant data capturing system. For example, the switch arrangement may be configured to be part of an input system for manipulating electronic settings or parameters of the data capturing unit 102. In certain embodiments, the data capturing unit 102 may be forced into a data input mode, whereafter signals from the switch arrangement may be used for shifting or modifying the electronic settings or parameters upon making or breaking of contacts within the switch arrangement. Hence, when a user urges the dose dial grip 122 towards a first rotational direction this may shift electronic settings or parameters in a first order or aspect whereas urging the dose dial grip 122 in the opposite direction may shift the electronic settings or parameters in a second order or aspect. Alternatively, the dose dial grip performs as a means for navigating through lists, such as menus on an electronic display. Thus, in such embodiments, the dose dial grip 122 may serve the dual purpose of manipulating the dose setting, i.e. the mechanical position of a dose setting element of the dose setting and expelling mechanism of the drug delivery unit 101, but also serve the purpose of manipulating an electronic setting other than a dose setting parameter or providing a means for navigating in an electronic user interface.

In the second embodiment, the dose dial grip 122 of the data capturing unit 102 defines an outer sleeve that rotationally slaves an inner sleeve of the data capturing unit 102. When the data capturing unit 102 is attached to the drug delivery unit 101, the inner sleeve attaches to the dose dial member of the drug delivery unit 101. However, in other embodiments, instead of having a dedicated inner sleeve of the data capturing unit 102, the torque transfer coupling may be configured for coupling directly to the dose dial member of the drug delivery unit 101, i.e. the dose dial member of the drug delivery unit 101 serves as a rotatable driven member or driven sleeve which is slaved by the dose dial grip 122.

In still other embodiments, the drug delivery unit 101 and data capture unit 102 may be arranged so as to be permanently fixed to each other, i.e. non-removably so as to provide a single integral system. In such single integral system the dose dial grip 122 performs as a drive sleeve, whereas an internal rotatable component, whose position is representative for the amount of drug to be expelled, performs as a rotatable driven member or driven sleeve wherein the torque transfer coupling couples rotation of the dose dial grip 122 with slaved and delayed rotation of the internal rotatable component.

While some embodiments according to the invention provides for tracking of dosage amounts, such as set dosage amounts or expelled dosage amounts, other more simple embodiments of a data capture unit of the drug delivery system according to the invention may be designed not to track information relating to dosage amounts but only provide data capture of time information relating to the occurrence of a dose setting activity and/or a dose expelling activity.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery system, comprising:
   an expelling structure for expelling an amount of drug from a reservoir, comprising:
   (a) a dose setting structure allowing a user to set a dose amount of drug to be expelled, and
   (b) an actuation structure for releasing or driving the drug expelling structure to expel the set dose amount,
   an electronically controlled capturing system for capturing data representing a property related to the amount of drug expelled from the reservoir by the expelling structure, and
   a switch structure coupled to the electronically controlled capturing system wherein operation of the switch structure initiates an action within the electronically controlled capturing system,
   wherein the dose setting structure comprises:
   a drive sleeve adapted to be rotated to set a dose,
   a rotatable driven member arranged for being rotationally driven by the drive sleeve, wherein a torque transfer coupling is arranged between the drive sleeve and the rotatable driven member for transferring rotational movement from the drive sleeve to the rotatable driven member,
   wherein the switch structure are coupled to the drive sleeve and the rotatable driven member, and
   wherein the torque transfer coupling is adapted to allow limited independent rotational movement of the drive sleeve relative to the rotatable driven member to operate the switch structure.

2. The drug delivery system as defined in claim 1, wherein the rotatable driven member defines or comprises a driven sleeve.

3. The drug delivery system as defined in claim 1, wherein the dose setting structure comprises a rotatable dose dial member, wherein the position of the dose dial member is representative for the amount of drug to be expelled, and wherein the dose dial member moves as the rotatable driven member is rotated.

4. The drug delivery system as defined in claim 1, wherein the rotatable driven member is rotatable in a first rotational direction to dial up a dose and wherein the rotatable driven member is rotatable in a second rotational direction counter to the first rotational direction to dial down an initially set dose.

5. The drug delivery system as defined in claim 1, wherein the rotatable driven member is arranged for rotation about an axis and wherein the drive sleeve is arranged coaxially with the rotatable driven member for rotation about said axis.

6. The drug delivery system as defined in claim 1, wherein rotation of the rotatable driven member requires exertion of a torque level above a first threshold torque and wherein said limited independent rotational movement requires exertion of a torque less than said first threshold torque.

7. The drug delivery system as defined in claim 1, wherein the dose setting structure defines a dose increment mechanism configured to provide for rotational movement of the rotatable driven member in discrete rotational steps through a multitude of rotational rest positions for the rotatable driven member.

8. The drug delivery system as defined in claim 1, wherein the switch structure is configured for starting initialization of the capturing system.

9. The drug delivery system as defined in claim 1, wherein the dose setting structure are configured so that a torque of a first magnitude are required to be exerted onto the rotatable driven member for movement of the rotatable driven member from a first rest position to a second neighbouring rest position and wherein said switch structure is configured to be operated for switching by exertion of a torque onto the drive sleeve of second magnitude less than said torque of first magnitude.

10. The drug delivery system as defined in claim 9, wherein upon increasing rotational torque onto the drive sleeve, exerted by the hand of a user, the capturing system is allowed to initialize in the course of an increase in rotational torque from said torque of second magnitude to said torque of first magnitude.

11. The drug delivery system as defined in claim 1, wherein the drive sleeve defines a pre-defined rotational rest position relative to the rotatable driven member and wherein the drive sleeve is movable relative to the rotatable driven member in at least one rotational direction away from said pre-defined rotational rest position to a rotational limit stop position by a movement less than 25 degrees.

12. The drug delivery system as defined in claim 11, further comprising a biasing structure arranged between the drive sleeve and the rotatable driven member, wherein the biasing structure urges the drive sleeve towards the pre-defined rotational rest position relative to the rotatable driven member.

13. The drug delivery system as defined in claim 11, wherein the movement is less than 10 degrees.

14. The drug delivery system as defined in claim 11, wherein the movement is less than 8 degrees.

15. The drug delivery system as defined in claim 11, wherein the movement is less than 6 degrees.

16. The drug delivery system as defined in claim 11, wherein the movement is less than 4 degrees.

17. The drug delivery system as defined in claim 11, wherein the movement is less than 2 degrees.

18. The drug delivery system as defined in claim 1, wherein the drive sleeve defines a pre-defined rotational rest position relative to the rotatable driven member, wherein the pre-defined rotational rest position is a pre-defined central rotational rest position and wherein the drive sleeve is movable relative to the rotatable driven member in either rotational direction away from said pre-defined central rotational rest position to a rotational limit stop position by a movement less than 25 degrees.

19. The drug delivery system as defined in claim 18, wherein the movement is less than 10 degrees.

20. The drug delivery system as defined in claim 18, wherein the movement is less than 8 degrees.

21. The drug delivery system as defined in claim 18, wherein the movement is less than 6 degrees.

22. The drug delivery system as defined in claim 18, wherein the movement is less than 4 degrees.

23. The drug delivery system as defined in claim 18, wherein the movement is less than 2 degrees.

24. The drug delivery system as in claim 1, comprising a drug delivery unit and a data capture unit releasably attachable to each other, the drug delivery unit comprising:
   the expelling structure,
   the actuation structure, and
   a rotatable dose dial member,
the data capture unit comprising:
   the drive sleeve,
   the rotatable driven member,
   the electronically controlled capturing system, and
   the switch structure,
wherein, when the drug delivery unit and the data capture unit are attached to each other, the rotatable driven member couples rotationally with the rotatable dose dial member so that the rotatable dose dial member rotates with the rotatable driven member.

25. The drug delivery system as in claim 24, wherein
   the data capture unit further comprises communication structure configured to transmit and/or receive information related to the captured data.

* * * * *